US00PP08404P

United States Patent [19]

de Ruiter

[11] Patent Number: Plant 8,404

[45] Date of Patent: Oct. 5, 1993

[54] HYBRID TEA ROSE PLANT NAMED RUIZESAC

[75] Inventor: Gijsbert de Ruiter, Hazerswoude, Netherlands

[73] Assignee: De Ruiter's Nieuwe Rozen B.V., Hazerswoude, Netherlands

[21] Appl. No.: 802,001

[22] Filed: Dec. 2, 1991

[51] Int. Cl.[5] ..... A01H 5/00

[52] U.S. Cl. ..... Plt./11

[58] Field of Search ..... Plt. 11, 12

[56] References Cited

U.S. PATENT DOCUMENTS

P.P. 5,846 1/1987 Kordes et al. ..... Plt. 20

P.P. 7,362 10/1990 de Ruiter ..... Plt. 18

*Primary Examiner*—Howard J. Locker

*Attorney, Agent, or Firm*—Christie, Parker & Hale

[57] ABSTRACT

A new variety of hybrid rose plant having red and silver bicolor flowers suitable for growing under glass.

2 Drawing Sheets

SUMMARY OF THE INVENTION

The present invention relates to a new and distinct variety of rose plant of the hybrid tea rose class, which was originated by me by crossing as the seed parent the variety known as 'Ruidriko' U.S. Plant Pat. No. 7,362, and as pollen parent the variety known as 'Korlingo', also known as 'Kardinal', U.S. Plant Pat. No. 5,846. The varietal denomination of the new variety is 'Ruizesac'.

Among the novel characteristics possessed by this new variety which distinguishes it from its parents and all other varieties of which I am aware are its red and silver bicolor flowers borne on a plant particularly suited for production of cut flowers under glass. The new variety can be reproduced through propagation by cuttings, grafting, budding and micropropagation, i.e. tissue culture. Flowers of the new variety are produced on long strong stems. Asexual reproduction by budding, grafting, propagation of cuttings, and micropropagation of the new variety as performed in Hazerswoude, Holland, shows that the foregoing and other distinguishing characteristics come true to form and are established and transmitted through succeeding propagations.

BRIEF DESCRIPTION OF ILLUSTRATIONS

The accompanying illustrations show typical specimens of the vegetative growth and flowers of the new variety in different stages of development depicted in color as nearly true as it is reasonably possible to make the same in a color illustration of this character. Colors may vary depending upon growing conditions under different climate, soil, and cultivation conditions.

One illustration shows cut flower form of the new variety and the other illustration shows details of the new rose variety with more accurate flower coloration.

DETAILED DESCRIPTION OF THE NEW VARIETY

The following is a detailed description of my new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart.

Parentage: Seedling.

*Seed parent.*—'Ruidriko'.

*Pollen parent.*—'Kardinal'.

Class: Hybrid tea.

As can be seen in the accompanying detailed illustration there is shown the top of a young shoot, 1; compound three, five and seven leaflet leaves, 2, 3, and 4 respectively; a stem, 5; bud, 6 and 7; a flower, 8, about one-third open; and a flower 9, more fully open. Also shown are flower stems 10, 11 and 12, with reproductive organs.

The following further horticultural observations were made of specimens grown under glass in Holland.

Flower

Blooming habit: Nearly continuous.

A. Bud:

(1) *Size.*—Medium.

(2) *Form.*—Ovoid (before separation of sepals); urn shaped after sepals part.

(3) *Color.*—As sepals divide, bud color is near 51B with near 51C washing; deeper red coloration at bud tip, near 45A.

(4) *Sepals.*—Shorter than bud, simple to slightly foliated.

(5) *Peduncle.*—Length — about medium. Aspect — straight. Strength — erect, very strong. Color — medium green near 137B to D.

B. Bloom:

*Flower.*—Medium to large size; viewed from above — round; viewed from side — (a) upper part of fully opened flower, flat; (b) lower part of fully opened flower, flat.

(1) *Size.*—Average size when fully expandede — about 11 to 12 cm.

(2) *Borne.*—Singly, one to a stem.

(3) *Form.*—Ovoid, spiral imbricated, becoming flat; recessed center; some outer petals reflex and quill to points; mid petals reflex and roll under slightly.

(4) *Petalage.*—Many petaled under normal condition — fully double about 40 petals.

(5) *Color.*—When sepals separate, near 51B with 51C washing and near 45A at bud end; when the sepals part and petals begin to unfurl, color of undersurface is near 51B to 52C with 50D and near 45A at petal edge; petals' top surface tends to near 50C to D, with deeper tone near 50A to B at end near petal edge in ⅓ to ½ open bloom. Deeper tonality appears only at petal edge in open flowers. Coloring at point of petal attachment is near 155D. Overall tonality from a distance is red-pink and silver reverse bicolor.

(6) *Pedicel.*—Few hairs or prickles.

(7) *Fragrance.*—Slight to none.

C. Petals:

(1) *Texture.*—Medium.

(2) *Appearance.*—Inside velvety and outside satiny.

(3) *Form and size.*—Large, transverse elliptic.

(4) *Arrangement.*—Regularly arranged, imbricated.

(5) *Petaloids in center.*—Few to none.

(6) *Lasting quality.*—Long lasting quality on plant and after cutting.

Reproductive Organs

A. Stamens, filaments and anthers:

*Arrangement and color.*—Regularly arranged around styles; color of filaments is pink.

B. Pollen:

*Color.*—Yellow orange.

C. Styles: Long, stigma above mouth of receptacle, red, only slightly hairy.

D. Stigmas: Positioned same level as anthers.

E. Hips: Urn, pitcher-shaped.

Plant

A. Form: Upright to bushy

B. Growth: Vigorous, about 1.7 m in height by about 45 cm in breadth.

C. Foliage: Compound 3, 5 and 7 leaflets (1) *Size.*—Large to very large.

(2) *Quantity.*—Abundant.

(3) *Color.*—Foliage at time of first flowering—near 137A to near 139A.

(4) *Shape.*—Oval, pointed.

(5) *Texture.*—Upper side is medium to strongly glossy; underside is matte.

(6) *Edge.*—Serrate.

(7) *Serration.*—Ordinary, acuminate apices.

(8) *Leaf stem.*—Color—medium green.

(9) *Stipules.*—Short, simple, medium to dark green, distinct auricle.

(10) *Leaflets.*—Cross section — flat; little or no undulation coloration —margin; terminal leaflet— medium length and width, rounded base; petiole— long.

D. Wood:

(1) *New wood.*—Color— young shoots have medium anthocyanin coloration— bronze.

(2) *Old wood.*—Color — medium green.

E. Prickles (Thorns):

(1) *Prickles.*—Present; quantity (main stalk) — ordinary; On laterals from stalk — ordinary; Shape of upper side— concave to flat; Shape of lower side — concave Length — $\leqq 5$ mm, very few; $>5$ mm, medium. Color — tan to reddish tan, depending in position on stem. irregular.

I claim:

1. A new and distinct variety of rose plant of the hybrid tea rose class, substantially as shown and described.

* * * * *

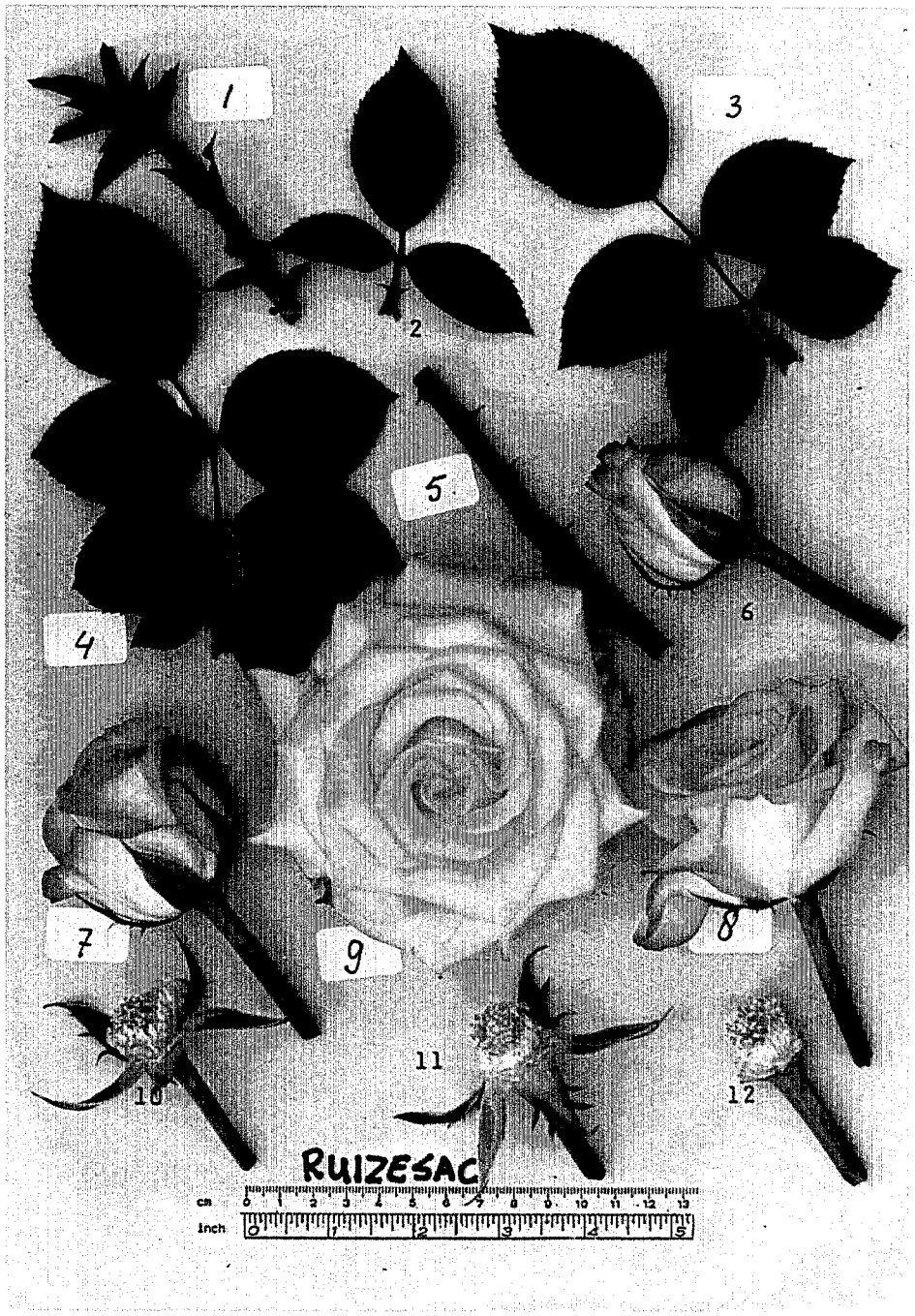
1
2
3
4
5
6
7
8
9
10
11
12
RUIZESAC
cm
inch

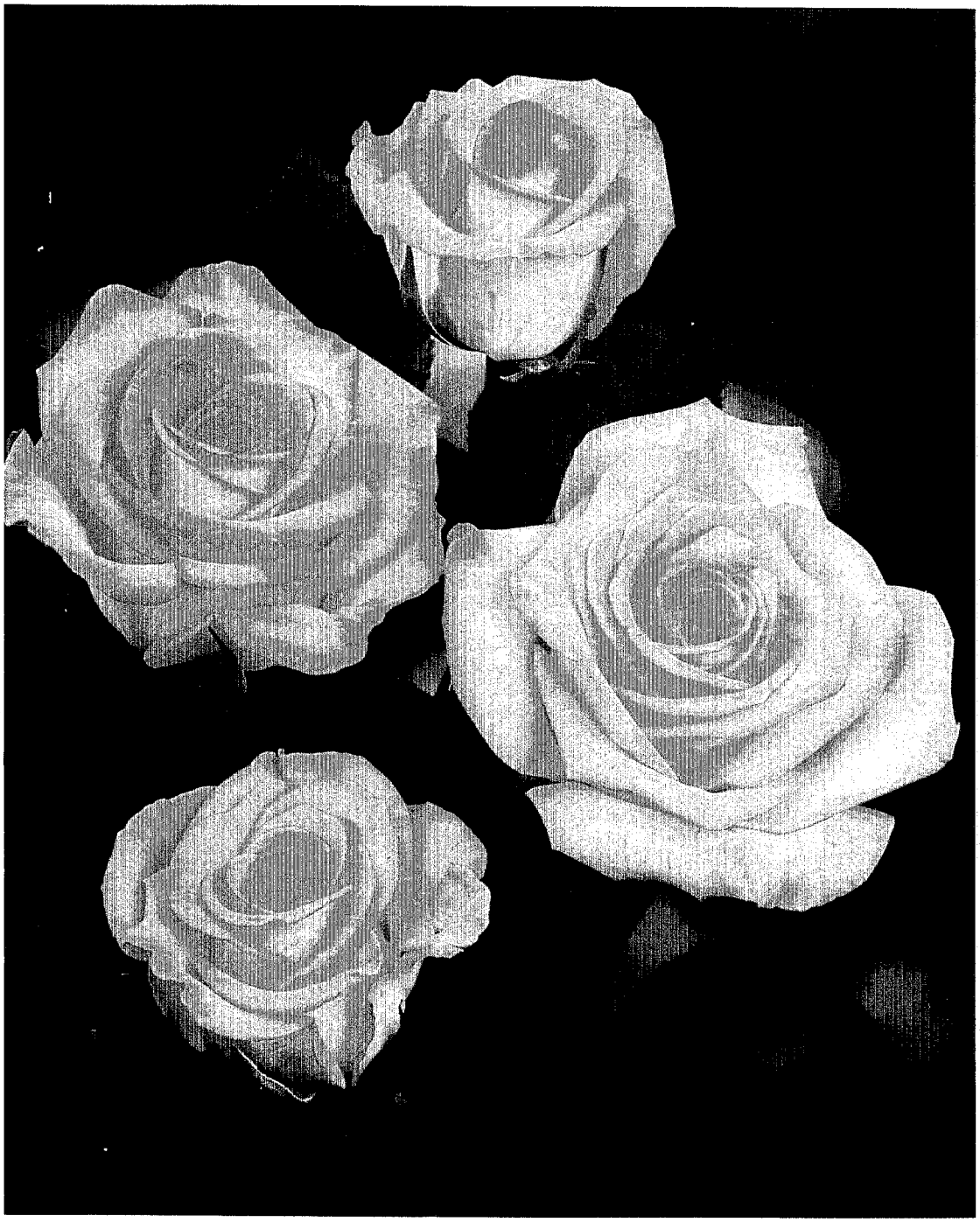

UNITED STATES PATENT AND TRADEMARK OFFICE

CERTIFICATE OF CORRECTION

PATENT NO. : Plant 8,404

DATED : October 5, 1993

INVENTOR(S) : Gijsbert de Ruiter

It is certified that error appears in the above-indentified patent and that said Letters Patent is hereby corrected as shown below:

Column 2, line 35, change "expandede" to -- expanded --.

Column 4, line 28, after "stem" insert --Position - irregular."--.

Signed and Sealed this

Thirtieth Day of August, 1994

*Attest:*

*Attesting Officer*

Bruce Lehman

BRUCE LEHMAN

*Commissioner of Patents and Trademarks*